United States Patent [19]

Moran et al.

[11] Patent Number: 4,569,934

[45] Date of Patent: Feb. 11, 1986

[54] IMIDAZO[1,2-b]PYRIDAZINES

[75] Inventors: Daniel B. Moran, Suffern, N.Y.; Dennis W. Powell, Greenwich, Conn.; Jay D. Albright, Nanuet, N.Y.

[73] Assignee: American Cyanamid Company, Stamford, Conn.

[21] Appl. No.: 658,716

[22] Filed: Oct. 9, 1984

[51] Int. Cl.⁴ .................. A61K 31/50; C07D 471/02; C07D 237/04; C07D 237/20

[52] U.S. Cl. .................. 514/248; 544/224; 544/236; 544/238; 544/241

[58] Field of Search .................. 544/236; 514/248

[56] References Cited

U.S. PATENT DOCUMENTS

| | | | |
|---|---|---|---|
| 3,489,755 | 1/1970 | Lombardino | 544/236 |
| 3,711,613 | 1/1973 | Tomcufcik et al. | 514/248 |
| 3,828,041 | 8/1974 | Tomcufcik et al. | 544/236 |
| 3,931,175 | 1/1976 | Perronnet et al. | 544/236 |
| 4,230,705 | 10/1980 | Allen, Jr. et al. | 544/236 |
| 4,353,903 | 10/1982 | Fabiani et al. | 514/248 |
| 4,464,372 | 8/1984 | Bristol et al. | 544/236 |

FOREIGN PATENT DOCUMENTS

| | | | |
|---|---|---|---|
| 57298D | 10/1980 | France. | |
| 40-22265 | 2/1965 | Japan | 544/236 |

*Primary Examiner*—Donald G. Daus
*Assistant Examiner*—Stephen M. Kapner
*Attorney, Agent, or Firm*—R. P. Raymond

[57] ABSTRACT

This invention concerns novel imidazo[1,2-b]-pyridazines and their use as agents for treating anxiety.

15 Claims, No Drawings

IMIDAZO[1,2-b]PYRIDAZINES

BRIEF SUMMARY OF THE INVENTION

This invention relates to new organic compounds and more particularly is concerned with novel imidazo[1,2-b]pyridazines which may be represented by the following general formula:

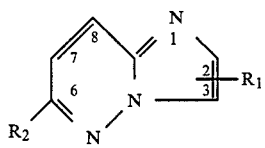

wherein $R_1$ is selected from the group consisting of hydrogen and lower alkyl having from 1 to 3 carbon atoms; and $R_2$ is selected from the group consisting of 3-pyridinyl and [3-(trifluoromethyl)phenyl] and the pharmacologically acceptable acid-addition salts thereof.

The invention also includes novel compositions of matter containing the above defined compounds which are useful as anxiolytic agents in mammals and the method of meliorating anxiety in mammals therewith.

Representative novel imidazo[1,2-b]pyridazine compounds included within the scope of the present invention are, for example:

3-Methyl-6-[3-(trifluoromethyl)phenyl]imidazo[1,2-b]pyridazine
3-Methyl-6-(3-pyridinyl)imidazo[1,2-b]pyridazine
2-Methyl-6-[3-(trifluoromethyl)phenyl]imidazo[1,2-b]pyridazine
2-Ethyl-6-[3-(trifluoromethyl)phenyl]imidazo[1,2-b]pyridazine
6-[3-(Trifluoromethyl)phenyl]imidazo[1,2-b]pyridazine
6-(3-Pyridinyl)imidazo[1,2-b]pyridazine
2-Methyl-6-(3-pyridinyl)imidazo[1,2-b]pyridazine
3-Ethyl-6-(3-pyridinyl)imidazo[1,2-b]pyridazine
3-Propyl-6-[3-(trifluoromethyl)phenyl]imidazo[1,2-b]pyridazine
2-Propyl-6-[3-(trifluoromethyl)phenyl]imidazo[1,2-b]pyridazine
2-Methyl-6-[3-(trifluoromethyl)phenyl]imidazo[1,2-b]pyridazine, hydrobromide The foregoing examples are illustrative of this invention and should not be construed to limit this invention in any way.

DETAILED DESCRIPTION OF THE INVENTION

The novel compounds of the present invention are obtainable, in general, as yellow to tan crystalline solids having characteristic melting points and absorption spectra. They are appreciably soluble in many organic solvents such as lower alkanols, chloroform, dichloromethane, tetrahydrofuran, N,N-dimethylformamide and the like, but are relatively insoluble in water.

The novel imidazo[1,2-b]pyridazines of the present invention may be readily prepared as set forth in the following reaction schemes:

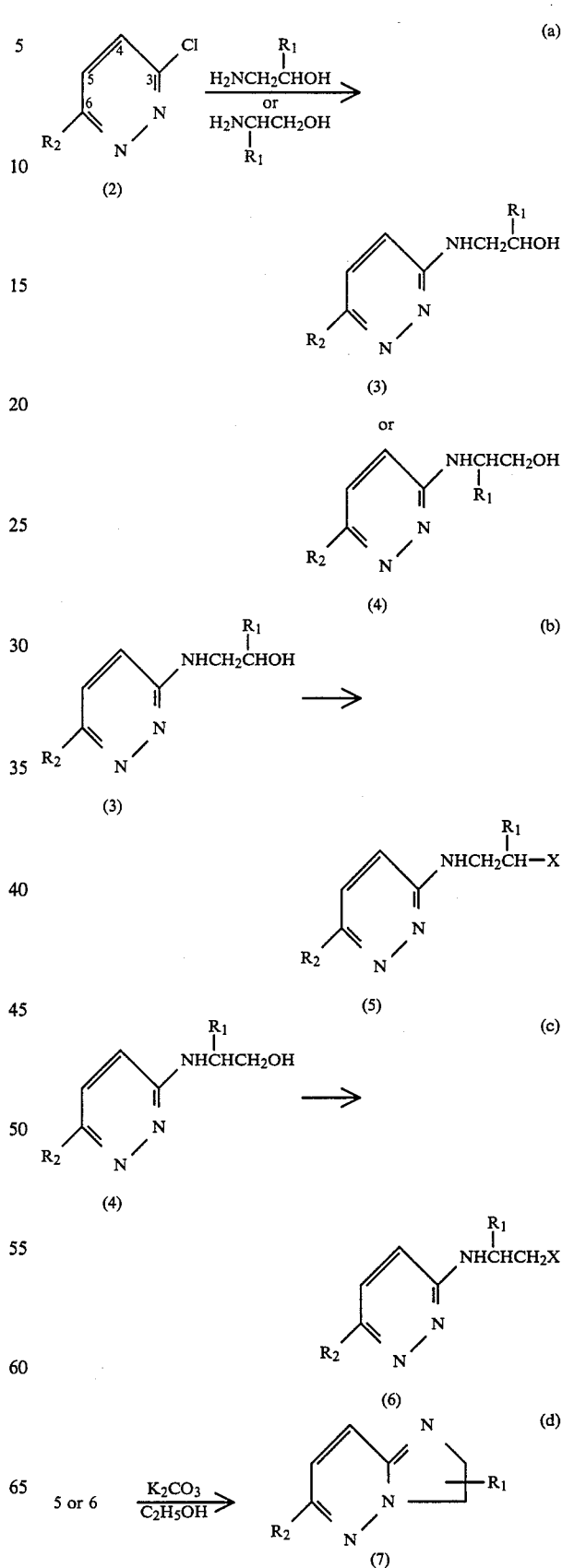

SCHEME I

SCHEME I -continued

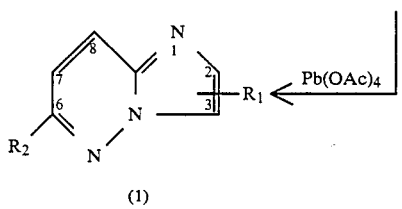

(1)

wherein $R_1$ and $R_2$ are as previously described and X is chlorine, bromine, —$OSO_2CH_3$, —$OSO_2CF_3$ or

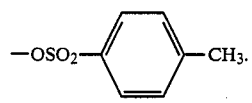

In accordance with Scheme I, 3-chloropyridazines substituted with a 3-pyridinyl or [3-(trifluoromethyl)-phenyl] group at the 6 position are reacted with 2-aminoethanols [$H_2NCH(R_1)CH_2OH$, $H_2NCH_2CH(R_1)OH$] wherein $R_1$ is hydrogen or a lower alkyl group having 1 to 3 carbon atoms to give 3-(2-hydroxyethylamino)pyridazines 3 and 4 (equation a). The 3-(2-hydroxyethylamino)pyridazines 3 and 4 are reacted with thionyl chloride to give the derivatives 5 and 6 wherein X is a chloro group. Ring closure of the 3-(2-chloroethylamino)pyridazines (5 and 6) affords intermediate 2,3-dihydroimidazo[1,2-b]pyridazines 7 which are converted with lead tetraacetate to the novel imidazo[1,2-b]pyridazines 1 of this invention.

The sequence of reactions shown in equations b and c may be combined into one step; that is the intermediates 5 and 6 may be cyclized in ethanol or lower alkanols with potassium carbonate to give the 2,3-dihydroimidazo[1,2-b]pyridazines 7 without isolation or purification.

The 3-(2-hydroxyethylamino)pyridazines 3 and 4 may be reacted with thionyl bromide or phosphorus tribromide to give the 3-(2-bromoethylamino)pyridazines (5 and 6; X=Br) or with methanesulfonyl chloride, trifluoromethylsulfonyl chloride, or p-toluenesulfonyl chloride to give derivatives 5 and 6 wherein X is —$OSO_2CH_3$, —$OSO_2CF_3$ or

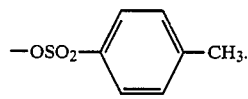

These derivatives and related ones which contain a leaving group X which can undergo nucleophilic displacement by the nitrogen atom of the pyridazine ring may be used in cyclization to give the intermediate 2,3-dihydroimidazo[1,2-b]pyridazines 7.

An alternative method for the preparation of imidazo[1,2-b]pyridazines 10 with lower alkyl groups in the C-2 position is illustrated in Scheme II. 3-Aminopyridazines 9, which are prepared as shown in equation e, react with α-haloketones such as bromoacetone, chloroacetone, 1-bromo-2-butanone, 1-chloro-2-butanone, 1-bromo-2-pentanone and the like to give directly, 2-lower alkyl imidazo[1,2-b]pyridazines 10.

SCHEME II

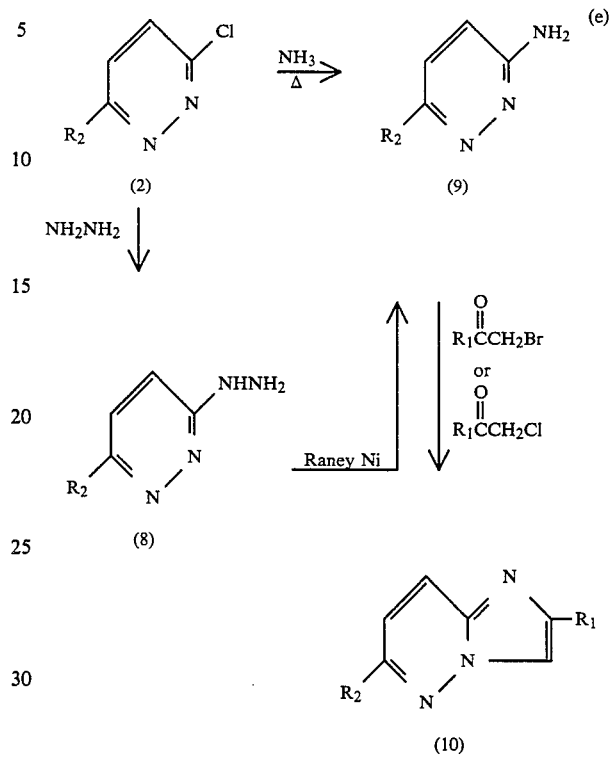

3-Lower alkyl imidazo[1,2-b]pyridazines may be prepared by reaction of 1-aminoketones 11 in which the ketone function is protected as the ethylene ketal derivative. Reaction of 3-chloropyridazines 2 with 1-aminoketone derivative 11 leads to pyridazine intermediates 12 which on cyclization in acetic acid or aqueous mineral acids give imidazo[1,2-b]pyridazines 13 substituted by lower alkyl groups at the C-3 position (Scheme III).

As illustrated in equation g (Scheme III) imidazo[1,2-b]pyridazines 13 may also be prepared by oxidation of the hydroxyl group of the side chain in 3-(hydroxyalkylamino)pyridazines 3 to a ketone function and cyclization of the intermediate 14 under thermal or preferably acid catalyzed conditions.

SCHEME III

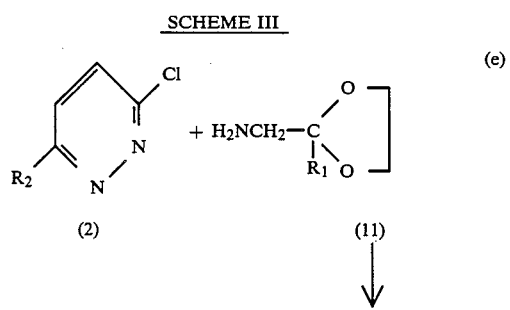

-continued
SCHEME III

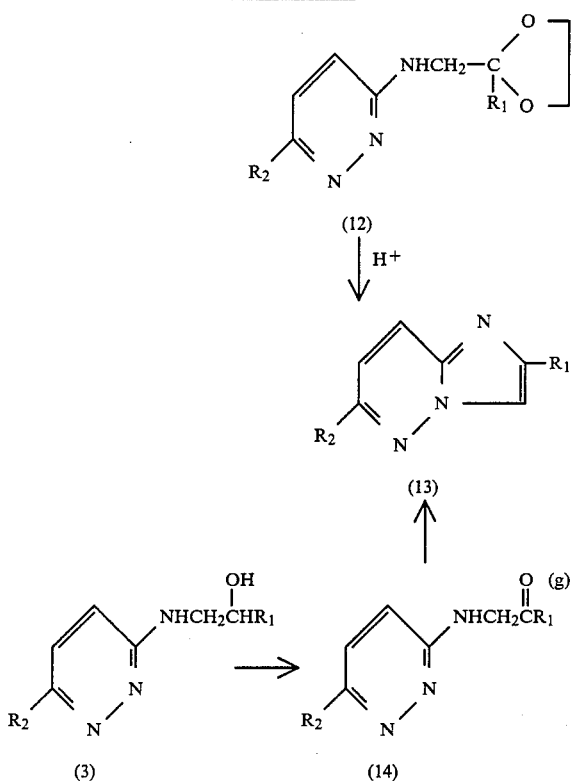

The antianxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle, containing 0.5% (v/v) polyethylene glycol and one drop of Polysorbate 80 to groups of at least four rats. At 30 or 60 minutes, the rats were treated intravenously with pentylenetetrazole at a dose of 23 mg/kg of body weight. This dose is estimated to cause clonic seizures in 99% of unprotected rats.

It has been reported [R. T. Hill and D. H. Tedeschi, "Animal Testing and Screening Procedures in Evaluating Psychotropic Drugs" in *An Introduction to Psychopharmacology*, Eds. R. R. Rech and K. E. Moore, Raven Press, New York, pp 237-288 (1971)] that there is a high degree of correlation between antagonism of pentylenetetrazole seizures in rats and antianxiety effects in higher warm-blooded animals.

The results in this test on representative compounds of this invention appear in Table I.

TABLE I

| Protection Against Clonic Seizures Caused by Pentylenetetrazole in Rats | | |
|---|---|---|
| Compound | Dose mg/kg | % of Rats Protected |
| 3-Methyl-6-[3-(trifluoromethyl)-phenyl]imidazo[1,2-b]pyridazine | 25 | 80 |
| 2-Methyl-6-[3-(trifluoromethyl)-phenyl]imidazo[1,2-b]pyridazine, hydrobromide | 50 | 75 |

Another test which has been used to assess antianxiety effects is a non-conditioned passive avoidance procedure described by J. R. Vogel, B. Beer and D. E. Clody, "A Simple and Reliable Conflict Procedure for Testing Antianxiety Agents", *Psychopharmacologia*, 21, 1-7 (1971). A conflict situation was induced in rats by a modification of this method.

Groups of 6 naive, Wistar strain rats, weighing 200-240 g each, were deprived of water for 48 hours and food for 24 hours. The test compounds were administered in single or graded, oral or intraperitoneal doses, suspended in a 2% starch vehicle containing 0.5% (v/v) polyethylene glycol and one drop of Polysorbate 80. Control animals received the vehicle alone. At 30 or 60 minutes each rat was placed in an individual plexiglass chamber. Water was available ad libitum from a tap located in the rear of the chamber. A 0.7 milliampere DC shocking current was established between the stainless steel grid floor and the tap. After 20 licks of non-shocked drinking, a shock was delivered for 2 seconds and then further shocks were delivered on a ratio of one shock for 2 seconds for every 20 licks. This was continued for a total of 3 minutes. The number of shocks taken by each rat during the 3 minute interval was recorded and compared to a control group.

The test compounds are considered active if the number of shocks received by the test group is significantly higher than the control group by the Mann-Witney U test.

The results of this test on representative compounds of this invention appear in Table II.

TABLE II

| Nonconditioned Passive Avoidance Test in Rats | | |
|---|---|---|
| Compound | Dose mg/kg | Result |
| 3-Methyl-6-[3-(trifluoromethyl)-phenyl]imidazo[1,2-b]pyridazine | 25 | Active |
| 3-Methyl-6-(3-pyridinyl)imidazo-[1,2-b]pyridazine | 25 | Active |
| 2-Methyl-6-[3-(trifluoromethyl)-phenyl]imidazo[1,2-b]pyridazine | 25 | Active |

The novel compounds of the present invention have been found to be useful for meliorating anxiety in mammals when administered in amounts ranging from about 0.1 mg to about 35.0 mg/kg of body weight per day. A preferred dosage regimen for optimum results would be from about 0.5 mg to about 5.0 mg/kg of body weight per day. Such dosage units are employed that a total of from about 35 mg to about 1.0 g of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example myristyl-gamma-picolinium chloride, benzalkonium chloride, phenethyl alcohol, p-chlorophenyl-alpha-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be compressed into tablets, or they may be incorporated directly with the food of the diet for oral therapeutic administration, the active compounds may be incorporated with excipients and used in the form of tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

SPECIFIC DISCLOSURE

The invention will be described in greater detail in conjunction with the following specific examples. The following examples are illustrative and should not be construed as limiting this invention in any way.

EXAMPLE 1

3-Methyl-6-(3-pyridinyl)imidazo[1,2-b]pyridazine

A 4.0 g sample of 3-chloro-6-(3-pyridinyl)pyridazine in 56 ml of 2-amino-1-propanol was heated at 140° C. for 8 hours. The solution was cooled, then poured into a mixture comprised of 200 ml of ether and 300 ml of water. The water layer was concentrated under vacuum and the 2-amino-1-propanol was removed by bulb to bulb distillation under high vacuum. The residue in 50 ml of thionyl chloride was refluxed for 0.5 hours then the volatiles were removed in vacuo. To the residue was added 150 ml of ethanol and 5 g of potassium carbonate. The mixture was refluxed for 4 hours. The solvent was evaporated in vacuo and the residue was partitioned between dichloromethane and water. The aqueous layer was extracted with three 50 ml portions of dichloromethane. The combined organic layers were dried over magnesium sulfate and the solvent was removed in vacuo. Ether was added to the residue and a brown solid was removed by filtration. The addition of hexane to the filtrate on chilling gave crystals which were recrystallized from ether-hexane to give 1.2 g of 2,3-dihydro-3-methyl-6-(3-pyridinyl)imidazo[1,2-b]pyridazine as orange crystals, mp 103.5°–105° C.

To a 0.83 g amount of the preceding compound in 50 ml of dichloromethane was added 3.5 g of lead tetraacetate. This mixture was stirred for one hour. The mixture was poured into a rapidly stirred solution of saturated sodium carbonate, diluted with 100 ml of water and extracted with three 50 ml portions of dichloromethane. The solvent was removed and the residue in dichloromethane was again treated with 1.8 g of lead tetraacetate for ½ hour. Work-up as before gave a yellow solid from the dichloromethane extract. The solid in ethyl acetate was passed through a short pad of hydrous magnesium silicate. The pad was washed with acetone and the combined acetone filtrate and wash was concentrated. The residue was crystallized from dichloromethane-hexane and gave 0.34 g of the product of the Example as yellow crystals, mp 173°–175° C.

EXAMPLE 2

3-Methyl-6-[3-(trifluoromethyl)phenyl]imidazo[1,2-b]pyridazine

A mixture of 5.18 g of 3-chloro-6-[3-(trifluoromethyl)phenyl]pyridazine and 4.60 g of aminoacetoneethyleneketal was heated at 150° C. under argon for 4 hours. The cooled mixture was dissolved in dichloromethane and the solution passed through a short pad of hydrous magnesium silicate. The filtrate was concentrated, diluted with hexane and chilled to give 0.8 g of crystals, mp 98°–100° C.

The preceding solid in 10 ml of glacial acetic acid was refluxed for 3 hours, then the volatiles were removed in vacuo. The residue in dichloromethane was dried over anhydrous sodium sulfate, then the solution was passed through a short pad of hydrous magnesium silicate. The filtrate was concentrated, diluted with hexane and chilled to give 0.32 g of the desired product as pale yellow crystals, mp 105°–107° C.

EXAMPLE 3

3-Methyl-6-[3-(trifluoromethyl)phenyl]imidazo[1,2-b]pyridazine

A 2.58 g sample of 3-chloro-6-[3-(trifluoromethyl)phenyl]pyridazine and 3.0 g of 1-amino-2-propanol was heated at 125° C. (internal temperature) for 5 hours, cooled and diluted with water. The mixture was extracted with dichloromethane (solid at interface). The mixture was filtered to give 2.5 g of solid which was crystallized from dichloromethane and gave 2.0 g of 1-methyl-2-[[6-(3-trifluoromethyl)phenyl]-3-pyridazinyl]amino ethanol as cream colored crystals, mp 132°–133° C.

A 2.7 g amount of the preceding compound (prepared as described above) and 20 ml of thionyl chloride was refluxed for ½ hour. The solvent was removed in vacuo. The residue was dissolved in 50 ml of ethanol, 2.5 g of potassium carbonate was added and the mixture was refluxed for 18 hours. One equivalent of cesium carbonate was added and the mixture was refluxed for 18 hours. The volatiles were removed in vacuo. Then dichloromethane was added and the mixture filtered. The filtrate was concentrated and the residue was crystallized from dichloromethane-hexane. Washing with dichloromethane gave 1.17 g of crystals which were recrystallized from dichloromethane-hexane to give 0.91 g of 2,3-dihydro-3-methyl-6-[3-(trifluoromethyl)phenyl]imidazo[1,2-b]pyridazine as white crystals, mp 250° C. (dec). An additional 1.5 g was recovered from the mother liquors.

A mixture of 3.55 g of the preceding compound (prepared as described above), 11.28 g of lead tetraacetate and 150 ml of dichloromethane was stirred for 3 hours. Then an additional 5.64 g of lead tetraacetate was added to the mixture and stirring was continued for 6 hours. The reaction mixture was poured into saturated sodium carbonate solution and diluted with water. This mixture was extracted with dichloromethane and the extracts were combined, dried over magnesium sulfate and concentrated in vacuo. The residue in ethyl acetate was passed through a short pad of hydrous magnesium silicate and the filtrate was concentrated. The residue was crystallized from dichloromethane-hexane to give 1.35 g of the product of the Example as pale yellow crystals, mp 105°–107° C.

EXAMPLE 4

3-Methyl-6-[3-(trifluoromethyl)phenyl]imidazo[1,2-b]pyridazine

A mixture of 1.46 ml of oxalyl chloride in 20 ml of dichloromethane was cooled to −78° C. under argon and 1.1 ml of dry dimethyl sulfoxide in 5 ml of dichloromethane was added rapidly. To the stirred mixture was added 0.5 g of 1-methyl-2-{[[6-(3-trifluoromethyl)phenyl]-3-pyridazinyl]amino}ethanol in 10 ml of dichloromethane and one ml of dimethyl sulfoxide. After stirring 15 minutes at −78° C., 0.726 ml of triethylamine was added in one portion and the mixture was stirred for 20 minutes. The mixture was allowed to warm to room temperature with stirring for one hour. The mixture was poured into a mixture of dichloromethane and saturated sodium carbonate. The organic layer was separated, dried over magnesium sulfate and filtered. The filtrate was evaporated in vacuo. The residue was crystallized from dichloromethane-hexane to give pale brown crystals, mp 159°–161° C. A mixture of the preceding compound in glacial acetic acid is refluxed for 3 hours to give the product of the Example as pale yellow crystals, mp 105°–107° C.

EXAMPLE 5

2-Methyl-6-[3-(trifluoromethyl)phenyl]imidazo[1,2-b]pyridazine

A mixture of 0.5 g of 3-chloro-6-[3-(trifluoromethyl)phenyl]pyridazine and 3 ml of 2-amino-1-propanol was heated at 130° C. for 24 hours, cooled and poured into water. The mixture was extracted with three 20 ml portions of dichloromethane. The combined extracts were washed with water, dried over magnesium sulfate and concentrated. The residual oil was dissolved in ethyl acetate and the solution passed through a short pad of silica gel. The filtrate was concentrated in vacuo and the residue was crystallized from dichloromethane-hexane to give 0.3 g of 2-[[6-[3-(trifluoromethyl)phenyl]-3-pyridazinyl]amino]-1-propanol as white crystals, mp 143°–144° C.

A mixture of 3.0 g of the preceding compound (prepared as described above) and 22 ml of thionyl chloride was refluxed for 45 minutes, then the solvent was removed in vacuo. The residue was partitioned between dichloromethane and saturated sodium carbonate. The organic layer was separated and the aqueous layer extracted with three 20 ml portions of dichloromethane. The organic layer and extracts were combined, dried over magnesium sulfate then the solvent was removed in vacuo. The residue was dissolved in 100 ml of ethanol, 2.6 g of potassium carbonate was added and the mixture refluxed for 2 hours. The solvent was removed in vacuo, dichloromethane was added and the mixture filtered. The filtrate was washed with 3% hydrochloric acid (2×250 ml). The aqueous layer was basified with 5N sodium hydroxide to pH 13 and extracted exhaustively with dichloromethane. The extract was dried and the solvent evaporated in vacuo to give 1.96 g of 2,3-dihydro-2-methyl-6-[3-(trifluoromethyl)phenyl]imidazo[1,2-b]pyridazine as an oil which crystallized as orange crystals, mp 86°–90° C.

A 1.16 g amount of the preceding compound, 3.68 g of lead tetraacetate and 50 ml of dichloromethane was stirred for 4 hours. An additional 1.84 g of lead tetraacetate was added and the mixture kept at 20° C. for two days. The mixture was poured into saturated sodium carbonate and extracted with dichloromethane. The combined extracts were dried over magnesium sulfate then concentrated in vacuo to give a brown oil. The oil in ethyl acetate was passed through a short pad of silica gel and through a short pad of hydrous magnesium silicate. The filtrate was concentrated and the residue triturated with ether to give tan crystals which were recrystallized from hexane. The mother liquors and ether triturate were combined and chromatographed on silica gel using ethyl acetate to give a solid which was recrystallized from hexane to give 0.55 g of the product of the Example as tan crystals, mp 128°–131° C.

EXAMPLE 6

2-Ethyl-6-[3-(trifluoromethyl)phenyl]imidazo[1,2-b]pyridazine

A 2.58 g sample of 3-chloro-6-[3-(trifluoromethyl)phenyl]pyridazine in 3.56 g of 2-amino-1-butanol was heated at 120° C. (internal temperature) for 18 hours, cooled and poured into cold water. The mixture was extracted with dichloromethane and the extracts washed with water, dried over anhydrous sodium sulfate and concentrated. The residue in ethyl acetate was chromatographed on silica gel with ethyl acetate to give 2.2 g of yellow oil. Crystallization from dichloromethane-hexane gave 2-{[6-[3-(trifluoromethyl)-phenyl]-3-pyridazinyl]amino}-1-butanol as crystals, mp 84°-87° C.

A 1.0 g sample of the preceding compound in 10 ml of thionyl chloride is refluxed for one hour, then the volatiles are removed in vacuo. The residue in 100 ml of ethanol and 2 g of potassium carbonate is refluxed for 2 hours then the volatiles removed in vacuo. The residue is partitioned between dichloromethane and water and the aqueous layer is extracted with dichloromethane. The combined organic layer is dried over magnesium sulfate and concentrated to give 2,3-dihydro-2-ethyl-6-[3-(trifluoromethyl)phenyl]imidazo[1,2-b]pyridazine.

Treatment of the preceding compound with lead tetraacetate in dichloromethane gives the product of the Example.

EXAMPLE 7

6-[3-(Trifluoromethyl)phenyl]imidazo[1,2-b]pyridazine

A mixture of 3.0 g of 3-chloro-6-[3-(trifluoromethyl)-phenyl]pyridazine and 2.93 g of 2-aminoethanol was heated at 120° C. for 18 hours, then cooled, diluted with cold water and stirred. Filtration gave a solid which was washed with water, then with hot chloroform. The chloroform filtrate was collected and concentrated and the residue was recrystallized from dichloromethane-hexane to give 2.0 g of 2-{[[6-(trifluoromethyl)phenyl]-3-pyridazinyl]amino}ethanol as cream crystals, mp 138°-139° C. A purified sample had mp 143°-144° C. (white needles).

A 2.86 g sample of the preceding compound (prepared as described above) and 22 ml of thionyl chloride was heated on a steam bath for 0.5 hours, then the volatiles removed in vacuo. The residue was dissolved in dichloromethane and poured into 200 ml of saturated sodium carbonate solution. The aqueous phase was extracted with dichloromethane and the organic extracts were combined, dried over magnesium sulfate and concentrated in vacuo. The residue was dissolved in 100 ml of ethanol, 1.5 g of potassium carbonate was added and the mixture was refluxed for 2 hours. The solvent was removed and the residue partitioned between dichloromethane and water. The organic layer was separated and the aqueous layer extracted with three 100 ml portions of dichloromethane. The organic layers were combined and extracted with 3% hydrochloric acid. The aqueous extract was basified with saturated sodium carbonate and extracted with dichloromethane. The dichloromethane extracts were combined, dried over magnesium sulfate and concentrated in vacuo. The residue was crystallized from dichloromethane-hexane to give 1.4 g of 2,3-dihydro-6-[3-(trifluoromethyl)phenyl]imidazo[1,2-b]pyridazine as orange crystals, mp 137°-139° C.

To a 1.6 g sample of the preceding compound in 50 ml of dichloromethane was added in one portion 5.35 g of lead tetraacetate. The solution was stirred for one hour. The solution was poured into a vigorously stirred saturated sodium carbonate solution, diluted with 100 ml of water and extracted with dichloromethane. The extracts were combined, dried over magnesium sulfate and passed through a short pad of hydrous magnesium silicate. The pad was washed with acetone to elute the product and the acetone wash was concentrated to give a solid which was chromatographed on silica gel with ethyl acetate to give 1.6 g of crystals. Recrystallization from dichloromethane-hexane first gave some black insoluble material which was removed by filtration through diatomaceous earth. Further cooling of the filtrate gave 1.5 g of the product of the Example as tan crystals, mp 98.5°-100.5° C.

EXAMPLE 8

6-(3-Pyridinyl)imidazo[1,2-b]pyridazine

A mixture of 2.0 g of 3-chloro-6-(3-pyridinyl)pyridazine and 25 ml of 2-aminoethanol is heated at 140° C. for 8 hours. As described for Example 1, the product is reacted with thionyl chloride and the obtained product ring closed to 2,3-dihydro-6-(3-pyridinyl)imidazo[1,2-b]pyridazine which is dehydrogenated to 6-(3-pyridinyl)imidazo[1,2-b]pyridazine.

EXAMPLE 9

2-Methyl-6-(3-pyridinyl)imidazo[1,2-b]pyridazine

A mixture of 5 g of 3-chloro-6-(3-pyridinyl)pyridazine and 30 ml of 2-amino-1-propanol is heated at 130° C. for 24 hours and the volatiles removed by bulb to bulb distillation under high vacuum to obtain the product 2-[[6-(3-pyridinyl)-3-pyridazinyl]amino]-1-propanol. As for Example 5, the preceding product is reacted with thionyl chloride and the obtained product is ring closed with potassium carbonate in ethanol to give 2,3-dihydro-2-methyl-6-(3-pyridinyl)imidazo[1,2-b]pyridazine which is dehydrogenated with lead tetraacetate to give 2-methyl-6-(3-pyridinyl)imidazo[1,2-b]pyridazine.

EXAMPLE 10

3-Ethyl-6-(3-pyridinyl)imidazo[1,2-b]pyridazine

A mixture of 5 g of 3-chloro-6-(3-pyridinyl)pyridazine and 30 ml of 2-amino-1-butanol is heated at 130° C. for 18 hours. Then the volatiles are removed by bulb to bulb distillation under high vacuum. As for Example 1, the product is reacted with thionyl chloride and the obtained product is ring closed with potassium carbonate in ethanol to give 2,3-dihydro-3-ethyl-6-(3-pyridinyl)imidazo[1,2-b]pyridazine which is dehydrogenated with lead tetraacetate in dichloromethane to give the desired product 3-ethyl-6-(3-pyridinyl)imidazo[1,2-b]pyridazine.

EXAMPLE 11

3-Propyl-6-[3-(trifluoromethyl)phenyl]imidazo[1,2-b]pyridazine

A mixture of 3.0 g of 3-chloro-6-[3-(trifluoromethyl)-phenyl]pyridazine and 5.0 g of 1-amino-2-pentanol is heated at 130° C. for 18 hours, cooled, diluted with water and extracted with dichloromethane. As for Example 3, the obtained product is reacted with thionyl chloride and the ring is closed with potassium carbonate in ethanol to give 2,3-dihydro-3-propyl-6-[3-(trifluoromethyl)phenyl]imidazo[1,2-b]pyridazine which is dehydrogenated with lead tetraacetate to give the product of the Example.

EXAMPLE 12

2-Propyl-6-[3-(trifluoromethyl)phenyl]imidazo[1,2-b[pyridazine

A mixture of 5.0 g of 3-chloro-6-[3-(trifluoromethyl)-phenyl]pyridazine and 10 g of 2-amino-1-pentanol is heated at 130° C. for 24 hours, cooled, poured into water and extracted with dichloromethane. As for Example 3, the obtained product is reacted with thionyl chloride and the ring is closed with potassium carbonate in ethanol to give 2,3-dihydro-2-propyl-6-[3-(trifluoromethyl)phenyl]imidazo[1,2-b]pyridazine which is dehydrogenated with lead tetraacetate to obtain the desired product.

EXAMPLE 13

2-Methyl-6-[3-(trifluoromethyl)phenyl]imidazo[1,2-b]pyridazine hydrobromide

A 12.5 g sample of 3-chloro-6-[3-(trifluoromethyl)-phenyl]pyridazine was placed in a steel cylinder with liquid ammonia and the sealed cylinder (bomb) was heated at 200° C. The chilled cylinder was opened and the ammonia allowed to evaporate. The solid residue was heated and stirred with chloroform, then filtered. The filtrate was concentrated and the residue recrystallized, first from chloroform-hexane, then twice from chloroform to give 1.8 g of 3-amino-6-[3-(trifluoromethyl)phenyl]pyridazine as white crystals, mp 143°–145° C.

Alternatively, 5.0 g of 3-hydrazino-6-[3-(trifluoromethyl)phenyl]pyridazine, 100 ml of ethanol, 10 ml of water and Raney nickel catalyst was shaken with hydrogen under 40 pounds of pressure in a Parr apparatus for 18 hours. The mixture was cooled and filtered and the filtrate concentrated to a gummy soid which was crystallized from dichloromethane-hexane to give 3-amino-6-[3-(trifluoromethyl)phenyl]pyridazine as off-white crystals, mp 138°–139° C.

A 1.5 g sample of 3-amino-6-[3-(trifluoromethyl)-phenyl]pyridazine, 1.23 g of bromoacetone and 50 ml of ethanol was refluxed for 18 hours. The volatiles were removed in vacuo and the residue dissolved in dichloromethane. The solution was treated with activated carbon, filtered, and concentrated. The residue was crystallized from dichloromethane-hexane to give 1.0 g of the desired product as cream colored crystals, mp 219°–221° C.

We claim:

1. A compound of the formula:

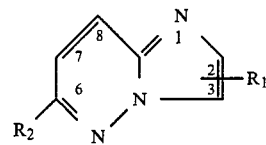

wherein $R_1$ is selected from the group consisting of hydrogen and lower alkyl having from 1 to 3 carbon atoms; and $R_2$ is selected from the group consisting of 3-pyridinyl and [3-(trifluoromethyl)phenyl] and the pharmacologically acceptable acid-addition salts thereof.

2. The compound, according to claim 1, 3-methyl-6-[3-(trifluoromethyl)phenyl]imidazo[1,2,-b]pyridazine.

3. The compound, according to claim 1, 3-methyl-6-(3-pyridinyl)imidazo[1,2,-b]pyridazine.

4. The compound, according to claim 1, 2-methyl-6-[3-(trifluoromethyl)phenyl]imidazo[1,2-b]pyridazine.

5. The compound, according to claim 1, 2-ethyl-6-[3-(trifluoromethyl)phenyl]imidazo[1,2-b]pyridazine.

6. The compound, according to claim 1, 6-[3-(trifluoromethyl)phenyl]imidazo[1,2,-b]pyridazine.

7. The compound, according to claim 1, 6-(3-pyridinyl)imidazo[1,2-b]pyridazine.

8. The compound, according to claim 1, 2-methyl-6-(3-pyridinyl)imidazo[1,2-b]pyridazine.

9. The compound, according to claim 1, 3-ethyl-6-(3-pyridinyl)imidazo[1,2-b]pyridazine.

10. The compound, according to claim 1, 3-propyl-6-[3-(trifluoromethyl)phenyl]imidazo[1,2-b]pyridazine.

11. The compound, according to claim 1, 2-propyl-6-[3-(trifluoromethyl)phenyl]imidazo[1,2-b]pyridazine.

12. The compound, according to claim 1, 2-methyl-6-[3-(trifluoromethyl)phenyl]imidazo[1,2-b]pyridazine, hydrobromide.

13. A method of meliorating anxiety in a mammal which comprises administering internally to said mammal a therapeutically effective amount of a compound of the formula as recited in claim 1.

14. An antianxiety composition of matter in dosage unit form which comprises a compound of the formula as recited in claim 1 in association with a pharmaceutically acceptable carrier.

15. An antianxiety composition of matter in dosage unit form which comprises a compound of the formula as recited in claim 1 in association with a pharmaceutically acceptable carrier and adjuvant.

* * * * *